(12) United States Patent
Le Breton et al.

(10) Patent No.: US 8,575,103 B2
(45) Date of Patent: Nov. 5, 2013

(54) PEPTIDES AND METHODS FOR INHIBITING G ALPHA PROTEIN SIGNALING

(75) Inventors: Guy Le Breton, Oak Park, IL (US); Jin-Sheng Huang, Oak Park, IL (US); Subhashini Srinivasan, Chicago, IL (US); Fadi T. Khasawneh, Rancho Cucamonga, CA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/425,922

(22) Filed: Mar. 21, 2012

(65) Prior Publication Data

US 2013/0040886 A1    Feb. 14, 2013

Related U.S. Application Data

(63) Continuation-in-part of application No. PCT/US2010/049905, filed on Sep. 23, 2010.

(60) Provisional application No. 61/350,093, filed on Jun. 1, 2010, provisional application No. 61/245,389, filed on Sep. 24, 2009.

(51) Int. Cl.
*A61K 38/00* (2006.01)
*A61K 38/08* (2006.01)
*C07K 7/08* (2006.01)
*C07K 7/06* (2006.01)
*C07K 9/00* (2006.01)
*A61P 7/02* (2006.01)

(52) U.S. Cl.
USPC .......... 514/13.8; 530/326; 530/328; 530/327; 530/322; 435/375; 514/21.5; 514/21.4; 514/21.6; 514/21.7

(58) Field of Classification Search
None
See application file for complete search history.

(56) References Cited

U.S. PATENT DOCUMENTS

| 7,419,779 B2 | 9/2008 | Lorens et al. .............. 435/4 |
| 2004/0053821 A1 | 3/2004 | Mosberg et al. ............. 514/20.6 |
| 2007/0065883 A1 | 3/2007 | Cockett et al. .............. 435/7.2 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Josef Vagner, Peptidomimetic, a synthetic tool of drug discovery, 2008, Curr Opin Chem Biol:12(3):292-296.*
Allison R. Nelson, Myristoyl-Based Transport of Peptides into Living Cells, 2007, Biochemistry, 46(51): pp. 14771-14781.*
Ngo et al, Computational Complexity, Protein Structure Protection, and the Levinthal Paradox, 1994, pp. 491-494.*
International Preliminary Report on Patentability from PCT/US2010/049905, Mar. 27, 2012.
Covic et al. "Pepducin-based Intervention of Thrombin-receptor Signaling and Systemic Platelet Activation" Nature Medicine 2002 8(10):1161-1165.
D'Ursi et al. "A Membrane-permeable Peptide Containing the Last 21 Residues of the $G\alpha_s$ Carboxyl Terminus Inhibits $G_s$-coupled Receptor Signaling in Intact Cells: Correlations between Peptide Structure and Biological Activity" Molecular Pharmacology 2006 69(3):727-736.
Freissmuth et al. "G Protein Antagonists" Trends in Pharmacological Sciences 1999 20(6):237-245.
Huang et al. "Signaling through $G\alpha_{13}$ Switch Region I Is Essential for Protease-activated Receptor 1-mediated Human Platelet Shape Change, Aggregation, and Secretion" The Journal of Biological Chemistry 2007 282(14):10210-10222.
Kuliopulos, A. and Covic, L. "Blocking Receptors on the Inside: Pepducin-based Intervention of PAR Signaling and Thrombosis" Life Sciences 2003 74(2-3):255-262.
Mazzoni et al. "A $G\alpha_s$ Carboxyl-terminal Peptide Prevents $G_s$ Activation by the $A_{2A}$ Adenosine Receptor" Molecular Pharmacology 2000 58(1):226-236.
Meigs et al. "Selective Uncoupling of $G\alpha_{12}$ from Rho-mediated Signaling" The Journal of Biological Chemistry 2005 280(18):18049-18055.
Nakamura et al. "Critical Role of Lysine 204 in Switch I Region of $G\alpha_{13}$ for Regulation of p115RhoGEF and Leukemia-associated RhoGEF" Molecular Pharmacology 2004 66(4):1029-1034.
Wells et al. "Identification of Potential Mechanisms for Regulation of p115 RhoGEF through Analysis of Endogenous and Mutant Forms of the Exchange Factor" The Journal of Biological Chemistry 2001 276(31):28897-28905.
International Search Report from PCT/US10/49905, Feb. 10, 2011.

\* cited by examiner

*Primary Examiner* — Julie Ha
*Assistant Examiner* — Erinne Dabkowski
(74) *Attorney, Agent, or Firm* — Licata & Tyrrell, P.C.

(57) ABSTRACT

Permeable Switch Region I and II peptides in the range of 9 to 25 amino acid residues in length are provided for specifically inhibiting signaling through Gα subunits. In addition, compositions and methods for inhibiting platelet aggregation and $\alpha_{11b}\beta_3$ integrin activation using the Switch Region I and II peptides are provided.

4 Claims, 4 Drawing Sheets

SEQUENCE LISTING

<160> NUMBER OF SEQ ID NOS: 34

<210> SEQ ID NO 1
<211> LENGTH: 6
<212> TYPE: PRT
<213> ORGANISM: Artificial Sequence

```
<220> FEATURE:
<223> OTHER INFORMATION: Synthetic peptide

<400> SEQUENCE: 1

Asn Ala Ala Ile Arg Ser
1               5

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide

<400> SEQUENCE: 2

Leu Leu Ala Arg Arg Pro Thr Ala Gly Ile His Glu Tyr
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Val Gly Gly Gln Arg Ser Glu Arg Arg Lys Trp Ile His Cys Phe Glu
1               5                   10                  15

Asn

<210> SEQ ID NO 4
<211> LENGTH: 17
<212> TYPE: PRT
<213> ORGANISM: Artificial Sequence
<220> FEATURE:
<223> OTHER INFORMATION: Synthetic peptide

<400> SEQUENCE: 4

Val Gly Gly Gln Arg Ser Glu Arg Lys Lys Trp Ile His Cys Phe Glu
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide

<400> SEQUENCE: 5

Val Gly Gly Gln Arg Ser Glu Arg Lys Arg Trp Phe Glu Cys Phe Asp
1               5                   10                  15

Ser

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide

<400> SEQUENCE: 6

Leu Ile Arg Pro Tyr Leu His Arg Ala Thr Lys Glu Gly
1               5                   10
```

```
<210> SEQ ID NO 7
<211> LENGTH: 17
<212> TYPE: PRT
<213> ORGANISM: Artificial Sequence
<220> FEATURE:
<223> OTHER INFORMATION: Synthetic peptide

<400> SEQUENCE: 7

Gln Arg Ile Ala Phe Cys Ser Glu Gly Val Glu Lys Gly His Trp Asn
1               5                   10                  15

Arg

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide

<400> SEQUENCE: 8

Gly Ile His Glu Trp Glu Val Gly Ser Phe Lys Gly Cys Gln Lys Arg
1               5                   10                  15

Arg

<210> SEQ ID NO 9
<211> LENGTH: 17
<212> TYPE: PRT
<213> ORGANISM: Artificial Sequence
<220> FEATURE:
<223> OTHER INFORMATION: Synthetic peptide

<400> SEQUENCE: 9

Gly Phe Asp Glu Trp Glu Val Ser Phe Lys Gly Cys Gln Arg Arg Ser
1               5                   10                  15

Arg

<210> SEQ ID NO 10
<211> LENGTH: 13
<212> TYPE: PRT
<213> ORGANISM: Artificial Sequence
<220> FEATURE:
<223> OTHER INFORMATION: Synthetic peptide

<400> SEQUENCE: 10

Leu Leu Ala Arg Arg Pro Thr Lys Gly Ile His Glu Tyr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

Arg Ser Glu Arg Lys Arg Trp Phe Glu Cys Phe Asp
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12
```

```
Ala Arg Arg Pro Thr Ala Gly Ile His Glu Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

Leu Leu Ala Arg Arg Pro Thr Ala Gly Ile His
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Ala Arg Arg Pro Thr Ala Gly Ile His Glu
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide

<400> SEQUENCE: 15

Arg Ser Glu Arg Lys Arg Trp Phe Glu Cys Phe Asp Ser
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Val Gly Gly Gln Arg Ser Glu Arg Lys Arg Trp Phe Glu Cys Phe
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Synthetic peptide

<400> SEQUENCE: 17

Arg Ser Glu Arg Arg Lys Trp Ile His Cys Phe Glu Asn
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide

<400> SEQUENCE: 18

Val Gly Gly Gln Arg Ser Glu Arg Arg Lys Trp Ile His Cys Phe
1               5                   10                  15
```

<210> SEQ ID NO 19
<211> LENGTH: 12
<212> TYPE: PRT
<213> ORGANISM: Artificial Sequence
<220> FEATURE:
<223> OTHER INFORMATION: Synthetic peptide

<400> SEQUENCE: 19

Arg Ser Glu Arg Arg Lys Trp Ile His Cys Phe Glu
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic peptide

<400> SEQUENCE: 20

Arg Ser Glu Arg Lys Lys Trp Ile His Cys Phe Glu Asn
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide

<400> SEQUENCE: 21

Val Gly Gly Gln Arg Ser Glu Arg Lys Lys Trp Ile His Cys Phe
1               5                   10                  15

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide

<400> SEQUENCE: 22

Arg Ser Glu Arg Lys Lys Trp Ile His Cys Phe Glu
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Synthetic peptide

<400> SEQUENCE: 23

Val Gly Gly Gln Arg Ser Glu Arg Lys Ala Trp Phe Glu Cys Phe Asp
1               5                   10                  15

Ser

<210> SEQ ID NO 24
<211> LENGTH: 18
<212> TYPE: PRT
<213> ORGANISM: Artificial Sequence
<220> FEATURE:
<223> OTHER INFORMATION: Synthetic peptide

<400> SEQUENCE: 24

Arg Cys Arg Val Leu Thr Ser Gly Ile Phe Glu Thr Lys Phe Gln Val
1               5                   10                  15

Asp Lys

<210> SEQ ID NO 25
<211> LENGTH: 17
<212> TYPE: PRT
<213> ORGANISM: Artificial Sequence
<220> FEATURE:
<223> OTHER INFORMATION: Synthetic peptide

<400> SEQUENCE: 25

Val Gly Gly Gln Arg Asp Glu Arg Arg Lys Trp Ile Gln Cys Phe Asn
1               5                   10                  15

Asp

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

<400> SEQUENCE: 26

Arg Ser Arg Met Pro Thr Thr Gly Ile
1               5

<210> SEQ ID NO 27
<211> LENGTH: 17
<212> TYPE: PRT
<213> ORGANISM: Artificial Sequence
<220> FEATURE:
<223> OTHER INFORMATION: Synthetic peptide

<400> SEQUENCE: 27

Val Gly Gly Gln Lys Ser Glu Arg Lys Lys Trp Ile His Cys Phe Glu
1               5                   10                  15

Asn

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Arg Ser Arg Asp Met Thr Thr Gly Ile
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic peptide

<400> SEQUENCE: 29

Val Gly Gly Gln Lys Ser Glu Arg Lys Lys Trp Ile His Cys Phe Glu
1               5                   10                  15

Asn

<210> SEQ ID NO 30
<211> LENGTH: 9
<212> TYPE: PRT
<213> ORGANISM: Artificial Sequence
<220> FEATURE:

```
<223> OTHER INFORMATION: Synthetic peptide

<400> SEQUENCE: 30

Arg Val Arg Val Pro Thr Thr Gly Ile
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide

<400> SEQUENCE: 31

Leu Ala Arg Lys Ala Thr Lys Gly Ile
1               5

<210> SEQ ID NO 32
<211> LENGTH: 17
<212> TYPE: PRT
<213> ORGANISM: Artificial Sequence
<220> FEATURE:
<223> OTHER INFORMATION: Synthetic peptide

<400> SEQUENCE: 32

Val Gly Gly Gln Arg Ser Gln Arg Gln Lys Trp Phe Gln Cys Phe Asp
1               5                   10                  15

Gly

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Arg Thr Arg Val Lys Thr Thr Gly Ile
1               5

<210> SEQ ID NO 34
<211> LENGTH: 17
<212> TYPE: PRT
<213> ORGANISM: Artificial Sequence
<220> FEATURE:
<223> OTHER INFORMATION: Synthetic peptide

<400> SEQUENCE: 34

Val Gly Gly Gln Arg Ser Glu Arg Lys Lys Trp Ile His Cys Phe Glu
1               5                   10                  15

Asp
```

PEPTIDES AND METHODS FOR INHIBITING G ALPHA PROTEIN SIGNALING

INTRODUCTION

This application is a continuation-in-part of PCT/US2010/049905, filed Sep. 23, 2010, which claims the benefit of priority from U.S. Provisional Application Ser. No. 61/350,092, filed Jun. 1, 2010, and from U.S. Provisional Application Ser. No. 61/245,389 filed Sep. 24, 2009, the content of each of which is herein incorporated by reference in its entirety.

This invention was made with government support under contract number HL24530 awarded by the National Institutes of Health. The government has certain rights in the invention.

BACKGROUND OF THE INVENTION

Cells possess multiple G protein signaling pathways that contribute to many different cellular responses, and the relative participation of these individual pathways in cell development, function, survival and disease is actively being investigated. However, there is a lack of suitable drugs which selectively interfere with specific G protein signaling events, and which can be applied to the study of intact cells and the treatment of disease. With the exception of receptor-derived peptides (Freissmuth, et al. (1999) *Trends Pharmacol. Sci.* 20:237-245; Kuliopulos & Covic (2003) *Life Sci.* 74:255-262; Covic, et al. (2002) *Nat. Med.* 8:1161-1165), and G protein α subunit C-terminal peptides (Freissmuth, et al. (1999) supra; D'Ursi, et al. (2006) *Mol. Pharmacol.* 69:727-36; Mazzoni, et al. (2000) *Mol. Pharmacol.* 58:226-236), which modulate receptor-G protein coupling, the field has for the most part been limited to drug candidates that interfere with different downstream kinases or other downstream effectors. However, the separate G protein pathways share many of these downstream targets, thereby making it challenging to modulate a specific cellular function associated with a certain G protein.

Switch I and II regions of Gα subunits are structurally and functionally analogous to those first described in the small GTPase Ras (Pai, et al. (1990) *EMBO J.* 8:2351-2359), while switch III region is unique to heterotrimeric G proteins. These switch regions are domains which undergo conformational changes during G protein activation induced by GDP-GTP exchange (Pai, et al. (1990) supra; Milburn, et al. (1990) *Science* 247:939-945; Tong, et al. (1991) *J. Mol. Biol.* 217:503-516; Sondek, et al. (1994) *Nature* 372:276-279; Lambright, et al. (1994) *Nature* 369:621-628; Coleman & Sprang (1998) *Biochemistry* 37:14376-14385). Furthermore, crystallization studies have revealed that the switch I region (SR1) contains critical sites for not only binding GTP, but also other subunits (Lambright, et al. (1994) supra). Consequently, this region is thought to be important for modulating activation of the α-subunit, as well as for regulating the affinity of the α-subunit for the β-subunits (Lambright, et al. (1994) supra). Other studies have established that the $G\alpha_{13}$ subunit is critical for $G_{13}$-mediated Rho activation (Gratacap, et al. (2001) *J. Biol. Chem.* 276:47906-47913; Ponimaskin, et al. (2000) *FEBS Lett.* 478:173-177; Kuner, et al. (2002) *Eur. J. Neurosci.* 16:2333-2341; Chen, et al. (2001) *Nat. Struct. Biol.* 8:805-809; Wells, et al. (2001) *J. Biol. Chem.* 276:28897-28905; Wells, et al. (2002) *J. Biol. Chem.* 277:1174-1181) presumably through its interaction with p115RhoGEF (Wells, et al. (2001) supra; Meigs, et al. (2005) *J. Biol. Chem.* 280:18049-18055; Nakamura, et al. (2004) *Mol. Pharmacol.* 66:1029-1034). Indeed, it has been found that $G\alpha_{13}$ binds both the RGS and DH domains of p115RhoGEF, and that this $G\alpha_{13}$ binding to p115RhoGEF increased its GTPase activity (Wells, et al. (2001) supra). Furthermore, the direct participation of SR1 and SR2 in this p115RhoGEF binding interaction was provided by studies (Meigs, et al. (2005) supra) demonstrating that replacement of the 196 to 203 sequence of $G\alpha_{12}$ SR1 (or the replacement of the 244 to 249 sequence of $G\alpha_{12}$ SR2) by the sequence Asn-Ala-Ala-Ile-Arg-Ser (SEQ ID NO:1) reduced $G\alpha_{12}$ binding to p115RhoGEF in vitro. In addition, it has been demonstrated that a single mutation, i.e., K204A of $G_{13}$ switch I region, impairs the regulatory function of $G\alpha_{13}$ on p115 and LARG RhoGEF in vitro activities (Nakamura, et al. (2004) supra). A p115RhoGEF-RGS-$G_{13}$ crystal structure model has also been described in which both SR1 and SR2 of $G\alpha_{13}$ are important for binding interactions with p115RhoGEF (Chen, et al. (2001) supra). Taken together, these results suggest that Gα switch regions are important for G protein downstream effector activation.

SUMMARY OF THE INVENTION

The present invention is a peptide of SEQ ID NO:2-5, 11-22 or 24-34, or a peptidomimetic, or fragment thereof. In some embodiments, the peptide, peptidomimetic or fragment is acetylated, glycosylated, biotinylated, or myristoylated. A pharmaceutical composition comprising such a peptide, peptidomimetic or fragment is further embraced by this invention, as are methods for inhibiting Gα subunit signaling, platelet aggregation and $\alpha_{IIb}\beta_3$ integrin activation using the same.

DETAILED DESCRIPTION OF THE INVENTION

Figure 1:
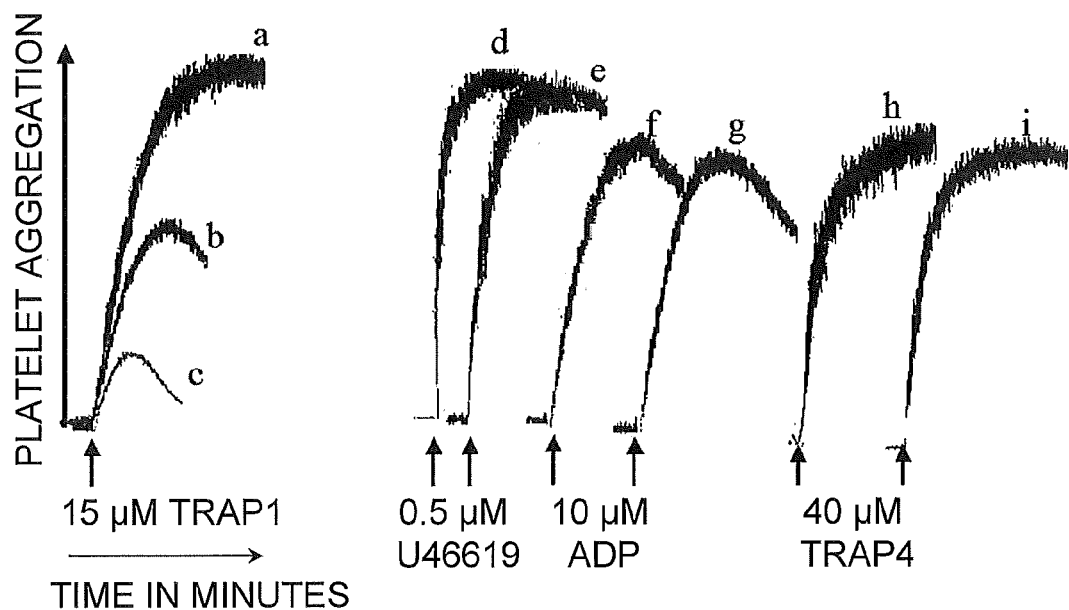
FIG. 1 shows the effects of Myr-$G_{13}$SR1$_{pep}$-2 (Myr-Leu-Leu-Ala-Arg-Arg-Pro-Thr-Ala-Gly-Ile-His-Glu-Tyr; SEQ ID NO:2) on human platelet aggregation. Trace (a) is control data from human platelet rich plasma (PRP) incubated with 500 μM of the Random Peptide (Myr-Leu-Ile-Arg-Pro-Tyr-Leu-His-Arg-Ala-Thr-Lys-Glu-Gly; SEQ ID NO:6), prior to stimulation with 15 μM of the PAR1 receptor agonist TRAP1. Trace (b) depicts data wherein PRP was treated with 30 μM Myr-$G_{13}$SR1$_{pep}$-2 prior to stimulation with 15 μM TRAP1. Trace (c) depicts data wherein PRP was treated with 50 μM Myr-$G_{13}$SR1$_{pep}$-2 prior to stimulation with 15 μM TRAP1. Trace (d) is control data showing PRP treated with 500 μM of the Random Peptide (SEQ ID NO:6) prior to stimulation with the 0.5 μM thromboxane receptor agonist U46619. Trace (e) depicts data wherein PRP was treated with 500 μM Myr-$G_{13}$SR1$_{pep}$-2 prior to stimulation with 0.5 μM U46619. Trace (f) is control data showing PRP treated with 500 μM of the Random Peptide (SEQ ID NO:6) prior to stimulation with 10 μM of the P2Y$_1$/P2Y$_{12}$ receptor agonist ADP. Trace (g) shows data wherein PRP was treated with 500 μM Myr-$G_{13}$SR1$_{pep}$-2 prior to stimulation with 10 μM ADP. Trace (h) depicts control data showing PRP treated with 500 μM of the Random Peptide (SEQ ID NO:6) prior to stimulation with 40 μM of the PAR4 receptor agonist TRAP4. Trace (i) depicts data wherein PRP was treated with 500 μM Myr-$G_{13}$SR1$_{pep}$-2 prior to stimulation with 40 μM TRAP4.
Figure 7:
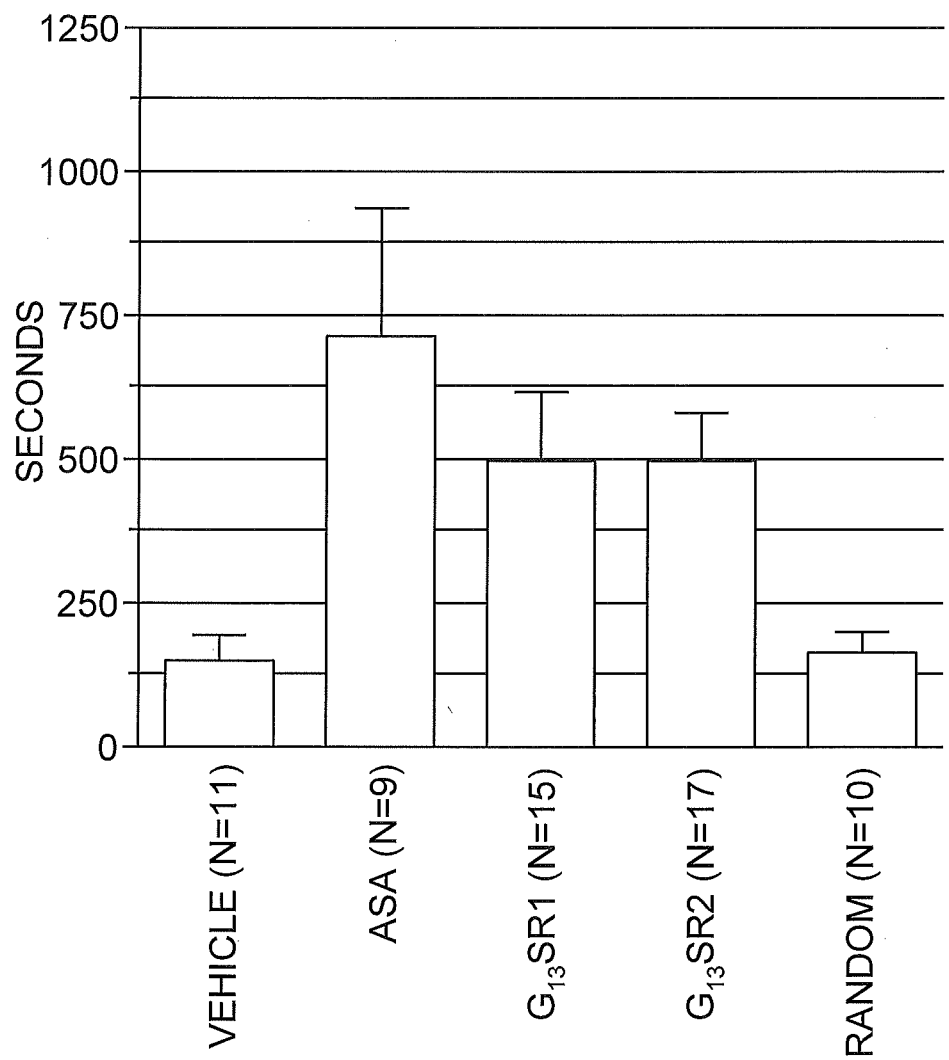
FIG. 7 shows the effects of intravenous administration of Myr-$G_{13}SR1_{pep}$-2 (Myr-Leu-Leu-Ala-Arg-Arg-Pro-Thr-Ala-Gly-Ile-His-Glu-Tyr; SEQ ID NO:2), $G_{13}SR2_{pep}$, (Val-Gly-Gly-Gln-Arg-Ser-Glu-Arg-Lys-Arg-Trp-Phe-Glu-Cys-Phe-Asp-Ser; SEQ ID NO:5), Random Peptide control (Myr-Leu-Ile-Arg-Pro-Tyr-Leu-His-Arg-Ala-Thr-Lys-Glu-Gly; SEQ ID NO:6), aspirin (ASA) or vehicle on bleeding times in mice. Briefly, CD1 mice (25 grams) were anesthetized with sodium pentobarbital, and either 100 μl of vehicle or 100 μl of a vehicle solution containing 3.7 mM of each peptide or aspirin was administered intravenously via the tail vein. Five minutes following administration, the tail was cut 0.5 cm from the tip and immersed in PBS buffer (pH 7.4; 37EC). Cessation of bleeding was observed visually and the total bleeding time was recorded. It can be seen that both Myr-$G_{13}SR1_{pep}$-2 and $G_{13}SR2_{pep}$ increased bleeding times relative to vehicle and Random peptide control, and that this increase appeared to be less than that caused by ASA administration.

Since the switch regions of the separate G protein classes possess different amino acid sequences, it was contemplated that SR1 and/or SR2 would represent sites for specific pharmacological modulation of G protein signaling. To demonstrate this, a permeable peptide Myr-$G_{13}SRI_{pep}$ (Myr-Leu-Leu-Ala-Arg-Arg-Pro-Thr-Lys-Gly-Ile-His-Glu-Tyr; SEQ ID NO:10) was designed, which represented the conformationally sensitive SR1 of the $G\alpha_{13}$ subunit (Huang, et al. (2007) *J. Biol. Chem.* 282:10210-10222). The effects of this peptide on human platelet signaling and function through thrombin PAR1 receptors, which are known to couple to $G\alpha_{13}$, were analyzed. It was found that Myr-$G_{13}SR1_{pep}$ selectively and dose-dependently inhibited PAR1-induced human platelet aggregation (Huang, et al. (2007) *J. Biol. Chem.* 282:10210-10222). In order to increase the potency of Myr-$G_{13}SR1_{pep}$, its amino acid sequence was modified such that the "Lys" residue was changed to "Ala". This modification resulted in a new peptide termed Myr-$G_{13}SR1_{pep}$-2 (Myr-Leu-Leu-Ala-Arg-Arg-Pro-Thr-Ala-Gly-Ile-His-Glu-Tyr; SEQ ID NO:2). Biological analysis of Myr-$G_{13}SR1_{pep}$-2 (SEQ ID NO:2) revealed a ten-fold increased potency relative to the original peptide (Myr-$G_{13}SR1_{pep}$) for inhibition of PAR1-induced human platelet aggregation. Specifically, treatment of human platelet-rich plasma (PRP) with 30-50 µM Myr-$G_{13}SR1_{pep}$-2 (SEQ ID NO:2) (but not the same concentrations of the Random Peptide (SEQ ID NO:6)) produced a progressive inhibition of the human platelet aggregation response (see FIG. 1). The selectivity of this inhibition for PAR1 signaling was further demonstrated by the finding that Myr-$G_{13}SR1_{pep}$-2 (SEQ ID NO:2) (even at 500 µM) had no measurable effect on aggregation induced by other platelet agonists which act on different receptors, i.e., adenosine diphosphate (ADP) acting at $P2Y_{12}$ and $P2Y_1$ receptors, U46619 acting at thromboxane $A_2$ receptors (TP) or TRAP1/TRAP4 acting at thrombin PAR1 and PAR4 receptors, respectively (FIG. 1). These findings indicate that $G\alpha_{13}$ SR1 serves as a specific target for modulation of PAR1-induced human platelet aggregation, and that drugs fashioned against this SR1 of $G\alpha_{13}$ can serve as a therapeutic means of modulating $G_{13}$ signaling in vivo. Therapeutic use is supported by the finding (FIG. 7) that administration of Myr-$G_{13}SR1_{pep}$-2 (Myr-Leu-Leu-Ala-Arg-Arg-Pro-Thr-Ala-Gly-Ile-His-Glu-Tyr; SEQ ID NO:2) substantially increases in vivo bleeding times in mice. This increased bleeding can be ascribed to inhibition of mouse endothelial cell PAR1 receptors, which are known to contribute to the adhesion of thrombi to a site of vascular damage (Leger, et al. (2006) *Circulation* 114:1070-1077).

The ability of Myr-$G_{13}SR1_{pep}$-2 (SEQ ID NO:2) to block human PAR1-induced platelet aggregation, but not aggregation induced by ADP, TP and PAR4 receptors, indicates an important characteristic of human platelet G protein coupled receptors, i.e., they preferentially signal through specific G proteins. Based on this consideration, it was reasoned that selective drug targeting of G proteins would provide a means of specifically modulating the signaling pathways of different platelet receptors. Specifically, since platelet receptors for ADP ($P2Y_1$), thromboxane $A_2$ (TP) and thrombin (PAR4) are known to signal through the G protein $G_q$ (Huang, et al. (2004) *Cell Signal* 16:521-533; Huang, et al. (2007) *J. Biol. Chem.* 282:10210-10222), specific drug targeting of this G protein would be expected to interfere with signaling through all of these latter platelet receptors. To demonstrate this, a membrane-permeable myristoylated peptide (Myr-Val-Gly-Gly-Gln-Arg-Ser-Glu-Arg-Arg-Lys-Trp-Ile-His-Cys-Phe-Glu-Asn; Myr-$G_qSR2_{pep}$; SEQ ID NO:3) representing the conformationally sensitive SR2 of the $G\alpha_q$ subunit was synthesized, characterized, and examined for its effects on human platelet signaling and function.

Figure 2:
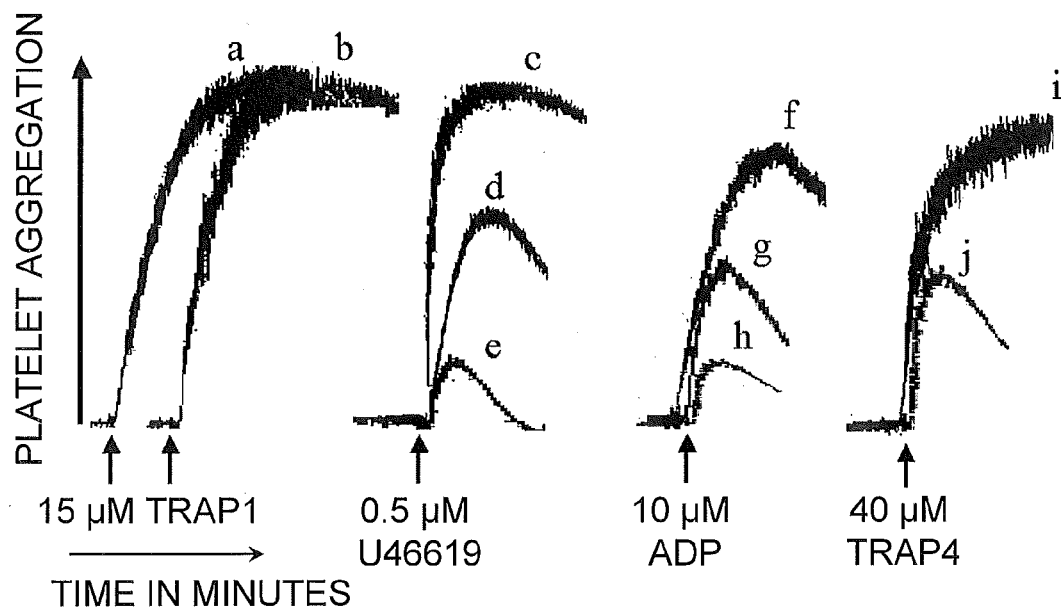
FIG. 2 shows the effects of Myr-$G_q$SR2$_{pep}$, (Myr-Val-Gly-Gly-Gln-Arg-Ser-Glu-Arg-Arg-Lys-Trp-Ile-His-Cys-Phe-Glu-Asn; SEQ ID NO:3) on human platelet aggregation. Trace (a) depicts control data showing PRP treated with 500 μM of the Random Peptide (Myr-Gln-Arg-Ile-Arg-Phe-Cys-Ser-Glu-Gly-Val-Glu-Lys-Gly-His-Trp-Asn-Arg; SEQ ID NO:7) prior to stimulation with 15 μM of the PAR1 receptor agonist TRAP1. Trace (b) depicts data wherein PRP was treated with 500 μM Myr-$G_q$SR2$_{pep}$ prior to stimulation with 15 μM TRAP1. Trace (c) is control data showing PRP treated with 500 μM Random Peptide (SEQ ID NO:7) prior to stimulation with the 0.5 μM of the thromboxane receptor agonist U46619. Trace (d) depicts data wherein PRP was treated with 50 μM Myr-$G_qSR2_{pep}$, prior to stimulation with 0.5 μM U46619. Trace (e) depicts data wherein PRP was treated with 150 μM Myr-$G_qSR2_{pep}$ prior to stimulation with 0.5 μM U46619. Trace (f) is control data showing PRP treated with 500 μM Random Peptide (SEQ ID NO:7) prior to stimulation with 10 μM ADP. Trace (g) depicts data wherein PRP was treated with 50 μM Myr-$G_qSR2_{pep}$ prior to stimulation with 10 μM ADP. Trace (h) depicts data wherein PRP was treated with 150 μM Myr-$G_qSR2_{pep}$ prior to stimulation with 10 μM ADP. Trace (i) is control data showing PRP treated with 500 μM Random Peptide (SEQ ID NO:7) prior to stimulation with 40 μM of the PAR4 receptor agonist TRAP4. Trace (j) depicts data wherein PRP was treated with 150 μM Myr-$G_qSR2_{pep}$ prior to stimulation with 40 μM of TRAP4.

The results demonstrated that Myr-$G_qSR2_{pep}$ (SEQ ID NO:3) (50-150 µM) produced a dose-dependent inhibition of human platelet aggregation induced by ADP, TP and PAR4 receptors (FIG. 2). Strikingly, Myr-$G_qSR2_{pep}$ was ineffective in blocking platelet aggregation induced by PAR1 receptor activation. Thus, the pharmacological profile of the anti-$G_q$ peptide (Myr-$G_qSR2_{pep}$; SEQ ID NO:3) was the mirror image of that associated with the anti-$G_{13}$ peptide (Myr-$G_{13}SR1_{pep}$-2; SEQ ID NO:2), which blocked PAR1 activation, but not activation due to ADP, U46619 or TRAP4.

Figure 3:
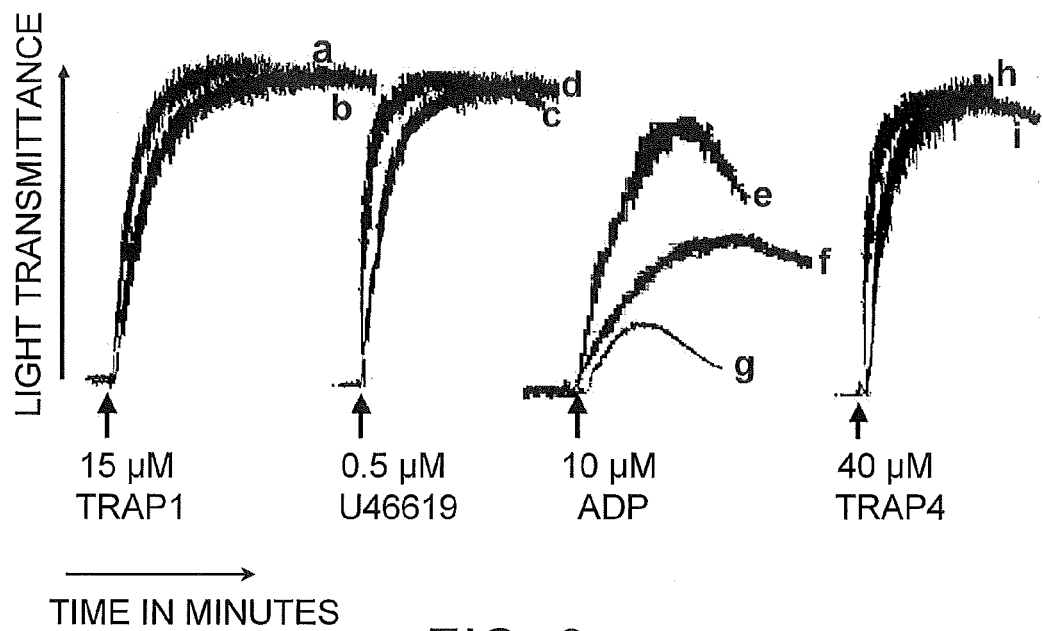
FIG. 3 shows the effects of Myr-$G_iSR2_{pep}$ (Myr-Val-Gly-Gly-Gln-Arg-Ser-Glu-Arg-Lys-Lys-Trp-Ile-His-Cys-Phe-Glu-Gly; SEQ ID NO:4) on human platelet aggregation. Trace (a) is control data showing PRP treated with 500 μM of the Random Peptide (Myr-Gly-Ile-His-Glu-Trp-Glu-Val-Gly-Ser-Phe-Lys-Gly-Cys-Gln-Lys-Arg-Arg; SEQ ID NO:8) prior to stimulation with 15 μM of the PAR1 receptor agonist TRAP1. Trace (b) depicts data wherein PRP was treated with 500 μM Myr-$G_iSR2_{pep}$ prior to stimulation with 15 μM TRAP1. Trace (c) is control data showing PRP treated with 500 μM Random Peptide (SEQ ID NO:8) prior to stimulation with the 0.5 μM of the thromboxane receptor agonist U46619. Trace (d) depicts data wherein PRP was treated with 500 μM Myr-$G_iSR2_{pep}$ prior to stimulation with 0.5 μM U46619. Trace (e) is control data showing PRP treated with 500 μM Random Peptide (SEQ ID NO:8) prior to stimulation with 10 μM ADP. Trace (f) depicts data wherein PRP was treated with 150 μM Myr-$G_iSR2_{pep}$, prior to stimulation with 10 μM ADP. Trace (g) depicts data wherein PRP was treated with 500 μM Myr-$G_iSR2_{pep}$ prior to stimulation with 10 μM ADP. Trace (h) is control data showing PRP treated with 500 μM Random Peptide prior (SEQ ID NO:8) to stimulation with 40 μM of the PAR4 receptor agonist TRAP4. Trace (i) depicts data wherein PRP was treated with 500 μM Myr-$G_iSR2_{pep}$ prior to stimulation with 40 μM of TRAP4

In addition to signaling through $G\alpha_q$, ADP is the only major platelet agonist known to signal through $G\alpha_i$ (Ohlmann, et al. (1995) *Biochem. J.* 15:775-779; Nieswandt, et al. (2000) *Blood* 96:2134-2139). Therefore, it was determined whether a specific peptide targeting $G\alpha_i$ selectively interferes with signaling induced by ADP without affecting signaling induced by TRAP1, U46619 or TRAP4. To demonstrate this selectivity, a membrane permeable myristolyated peptide (Myr-Val-Gly-Gly-Gln-Arg-Ser-Glu-Arg-Lys-Lys-Trp-Ile-His-Cys-Phe-Glu-Gly; Myr-$G_i$ $SR2_{pep}$; SEQ ID NO:4) representing the conformationally sensitive switch region 2 of the $G\alpha_i$ subunit was evaluated for its effects on human platelet aggregation. As illustrated in FIG. 3, Myr-$G_i$ $SR2_{pep}$, produced dose-dependent (150-500 µM) inhibition of ADP-induced aggregation without affecting aggregation caused by either TRAP1, U46619 or TRAP4, even at the highest concentration of Myr-$G_i$ $SR2_{pep}$ used, i.e., 500 µM.

Collectively, these results demonstrate pharmacological inhibition of the signaling through specific G proteins with peptides that target (or mimic) the conformationally sensitive switch regions of the $G\alpha$ subunits. In particular, three different switch region peptides, i.e., Myr-$G_{13}SR1_{pep}$-2 (SEQ ID NO:2), Myr-$G_qSR2_{pep}$ (SEQ ID NO:3) and Myr-$G_i$ $SR2_{pep}$ (SEQ ID NO:4) were shown to possess three different pharmacological profiles. Importantly, these profiles are completely consistent with the known signaling pathways for each of the G proteins which they selectively target. In this respect, the availability of such selective drugs for the different G proteins could significantly impact the therapy of multiple human disease states.

While different G protein-coupled receptors are known to signal through certain G proteins and specific downstream pathways, it is also known that many G protein-coupled receptors can activate a common signaling target. For example, all platelet stimulating G protein-coupled receptors, i.e., ADP, TP, PAR1, PAR4, etc., cause activation of $\alpha_{11b}\beta_3$ integrin, which is the basis for their ability to induce platelet aggregation. One underlying mechanism of this process, involving a common effector component, has now been identified. Specifically, the present data demonstrate that a non-myristolyated amino acid sequence representing $G\alpha_{13}$ SR2 effectively inhibits human platelet aggregation and $\alpha_{11b}\beta_3$ integrin activation induced by all major platelet agonist G protein-coupled receptors, indicating that this peptide has a mechanism of action that affects the final common pathway of $\alpha_{IIb}\beta_3$ integrin activation.

Figure 4:
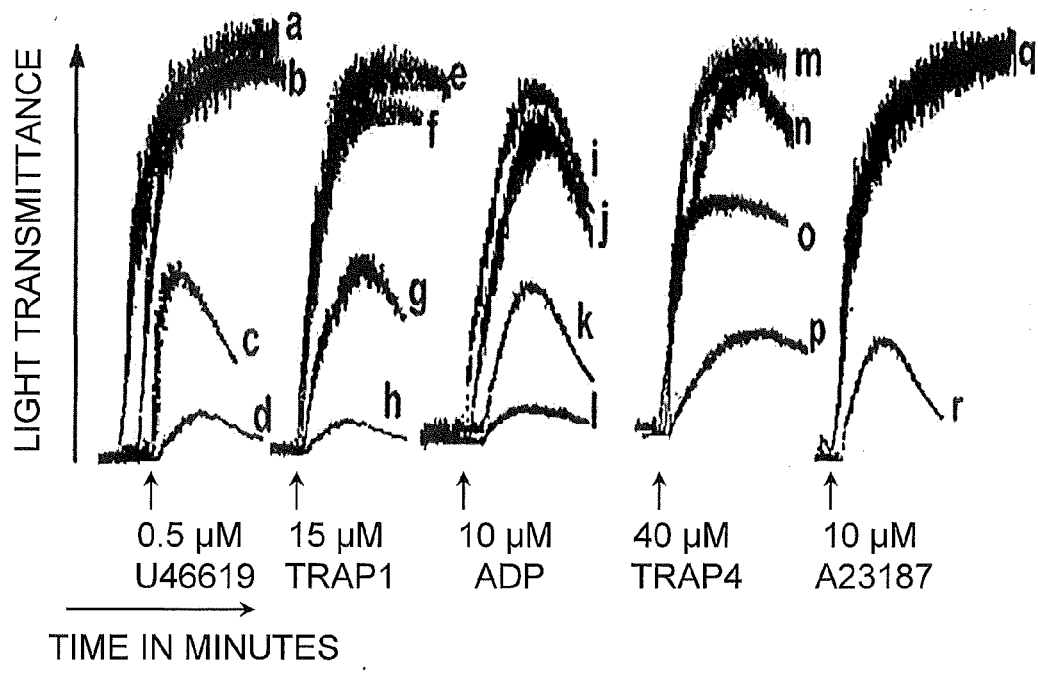
FIG. 4 shows the effects of $G_{13}$ Switch Region 2 peptide ($G_{13}SR2_{pep}$: Val-Gly-Gly-Gln-Arg-Ser-Glu-Arg-Lys-Arg-Trp-Phe-Glu-Cys-Phe-Asp-Ser; SEQ ID NO:5) on human platelet aggregation. Trace (a) is control data showing PRP treated with 500 μM of the Random Peptide (Gly-Phe-Asp-Glu-Trp-Glu-Val-Ser-Phe-Lys-Gly-Cys-Gln-Arg-Arg-Ser-Arg; SEQ ID NO:9) prior to stimulation with 0.5 μM of the thromboxane receptor agonist U46619. Trace (b) depicts data wherein PRP was treated with 75 μM $G_{13}SR2_{pep}$ prior to stimulation with 0.5 μM U46619. Trace (c) depicts data wherein PRP was treated with 100 μM $G_{33}SR2_{pep}$, prior to stimulation with 0.5 μM U46619. Trace (d) depicts data wherein PRP was treated with 150 μM $G_{13}SR2_{pep}$ prior to stimulation with 0.5 μM U46619. Trace (e) is control data showing PRP treated with 500 μM of the Random Peptide (SEQ ID NO:9) prior to stimulation with 15 μM of the PAR1 receptor agonist TRAP1. Trace (f) depicts data wherein PRP was treated with 75 μM $G_{13}SR2_{pep}$ prior to stimulation with 15 μM TRAP1. Trace (g) depicts data wherein PRP was treated with 100 μM $G_{13}SR2_{pep}$, prior to stimulation with 15 μM TRAP1. Trace (h) depicts data wherein PRP was treated with 150 μM $G_{13}SR2_{pep}$, prior to stimulation with 15 μM TRAP1. Trace (i) is control data showing PRP treated with 500 μM of the Random Peptide (SEQ ID NO:9) prior to stimulation with 10 μM ADP. Trace (j) depicts data wherein PRP was treated with 75 μM $G_{13}SR2_{pep}$, prior to stimulation with 10 μM ADP. Trace (k) depicts data wherein PRP was treated with 100 μM $G_{13}SR2_{pep}$ prior to stimulation with 10 μM ADP. Trace (l) depicts data wherein PRP was treated with 150 μM $G_{13}SR2_{pep}$, prior to stimulation with 10 μM ADP. Trace (m) is control data showing PRP treated with 500 μM of the Random Peptide (SEQ ID NO:9) prior to stimulation with 50 μM of the PAR4 receptor agonist TRAP4. Trace (n) depicts data wherein PRP was treated with 75 μM $G_{13}SR2_{pep}$ prior to stimulation with 50 μM of TRAP4. Trace (o) depicts data wherein PRP was treated with 100 μM $G_{13}SR2_{pep}$ prior to stimulation with 50 μM of TRAP4. Trace (p) depicts data wherein PRP was treated with 150 μM $G_{13}SR2_{pep}$, prior to stimulation with 50 μM of TRAP4. Trace (q) is control data showing PRP treated with 500 μM of the Random Peptide (SEQ ID NO:9) prior to stimulation with 10 μM of the ionophore A23187. Trace (r) depicts data wherein PRP was treated with 150 μM $G_{13}SR2_{pep}$ prior to stimulation with 10 μM of the ionophore A23187. The high degree of specificity of $G_{13}$ Switch Region 2 peptide sequence ($G_{13}SR2_{pep}$: Val-Gly-Gly-Gln-Arg-Ser-Glu-Arg-Lys-Arg-Trp-Phe-Glu-Cys-Phe-Asp-Ser; SEQ ID NO:5) was demonstrated by the finding that a single amino acid substitution of this sequence at amino acid 232 (from Arg to Ala; $G_{13}SR2_{mutant\,pep}$: Val-Gly-Gly-Gln-Arg-Ser-Glu-Arg-Lys-Ala-Trp-Phe-Glu-Cys-Phe-Asp-Ser; SEQ ID NO:23) completely eliminated the ability of the parent peptide ($G_{13}SR2_{pep}$) to block platelet and integrin activation.
Figure 5:
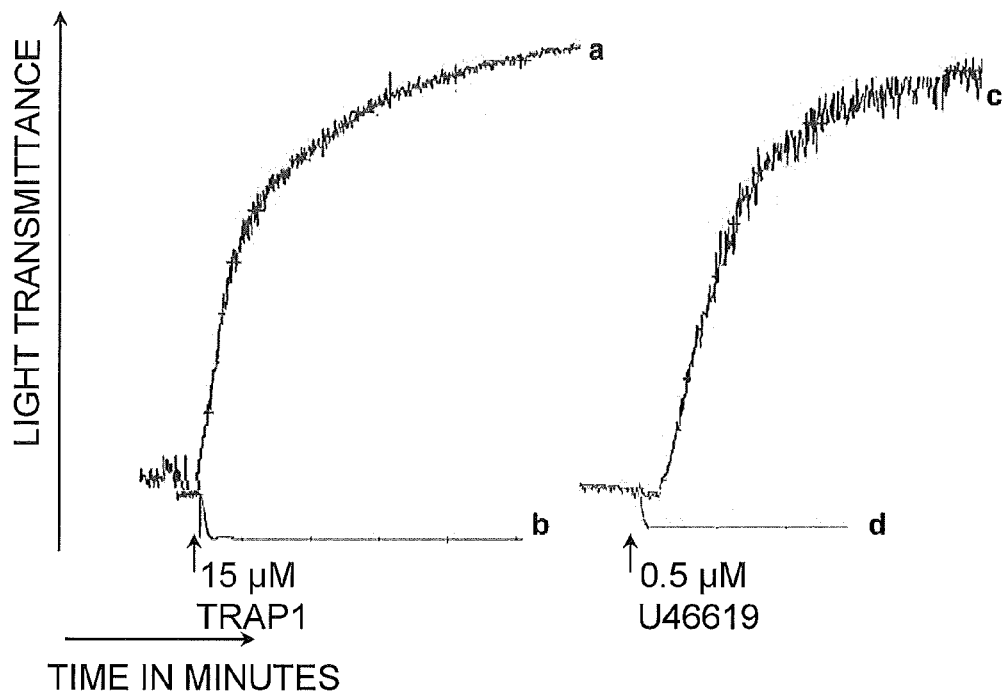
FIG. 5 shows the effects of the truncated version of the $G_{13}$ Switch Region 2 peptide ($G_{13}SR2_{pep-truncated}$: Arg-Ser-Glu-Arg-Lys-Arg-Trp-Phe-Glu-Cys-Phe-Asp; SEQ ID NO:11) on human platelet aggregation. Trace (a) shows PRP treated with 15 μM of the thrombin receptor agonist TRAP1 alone. Trace (b) depicts data wherein PRP was treated with 150 μM of $G_{13}SR2_{pep-truncated}$ prior to stimulation with 15 μM TRAP1. Trace (c) shows PRP treated with 0.5 μM of the thromboxane receptor agonist U46619 alone. Trace (d) depicts data wherein PRP was treated with 150 μM of $G_{13}SR2_{pep-truncated}$ prior to stimulation with 0.5 μM U46619.

In this respect, FIG. 4 illustrates that 75-150 µM $G_{13}SR2_{pep}$ (Val-Gly-Gly-Gln-Arg-Ser-Glu-Arg-Lys-Arg-Trp-Phe-Glu-Cys-Phe-Asp-Ser; SEQ ID NO:5) produced a dose-dependent inhibition of human platelet aggregation stimulated by U46619, TRAP1, ADP and TRAP4, whereas the Random Peptide (SEQ ID NO:9) was without effect. Furthermore, it was also shown that $G_{13}SR2_{pep}$ (SEQ ID NO:5) was capable of blocking platelet aggregation induced by the divalent cation ionophore A23187, confirming the universal nature of its inhibitory mechanism. In similar experiments, a twelve amino acid peptide, $G_{13}SR2_{pep-truncated}$ (Arg-Ser-Glu-Arg-Lys-Arg-Trp-Phe-Glu-Cys-Phe-Asp, SEQ ID NO:11; 150 µM), inhibited human platelet aggregation with the same potency as the full length sequence of $G_{13}SR2_{pep}$ peptide (SEQ ID NO:5) (FIG. 5). These results demonstrate that truncating the full length sequence of $G_{13}SR2_{pep}$, does not necessarily reduce its ability to inhibit human platelet aggregation. On the other hand, a single amino acid within the sequence of $G_{13}SR2_{pep}$, i.e., Arg232, is critical for the ability of this peptide to block integrin activation.

Figure 6:
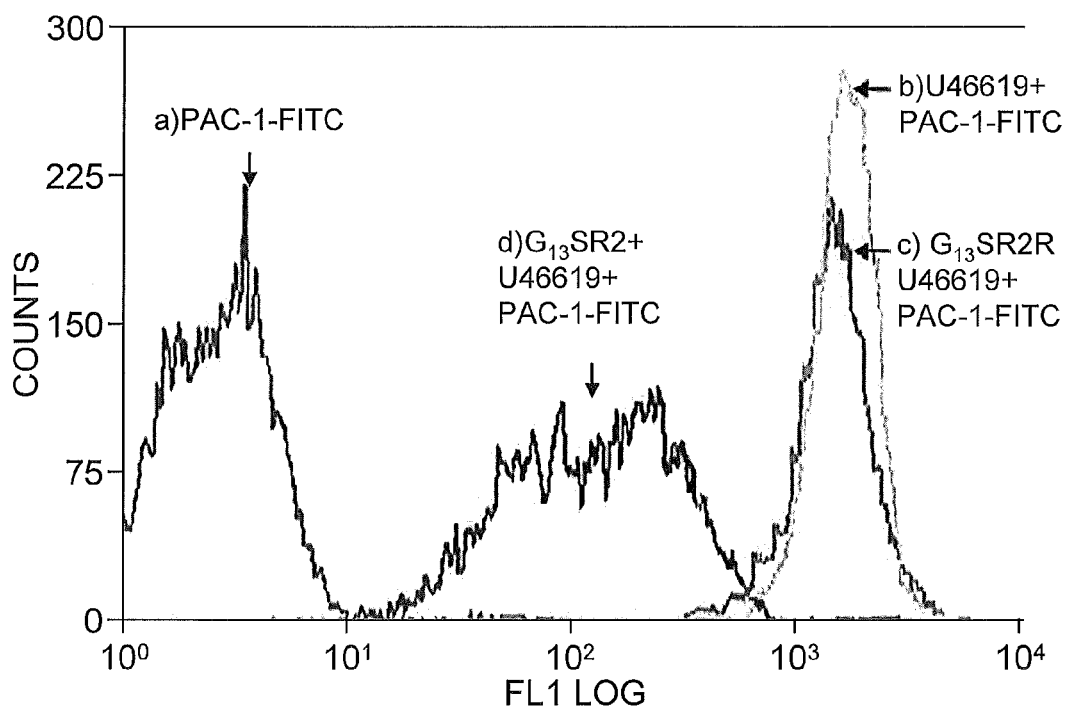
FIG. 6 shows the effects of $G_{13}SR2_{pep}$, (SEQ ID NO:5) on human platelet $\alpha_{11b}\beta_3$ integrin activation. The platelet count in human PRP was adjusted to $1\times10^6$ platelets/ml. The platelets were then labeled with FITC-conjugated PAC1 antibody against activated $\alpha_{11b}\beta_3$ integrin, and the samples were analyzed by flow cytometry in a Beckman Coulter CyAn II Flow Cytometer. Trace (a) depicts resting platelets labeled with FITC-PAC-1 antibody. Trace (b) depicts platelets stimulated with 0.5 μM U46619 and labeled with FITC-PAC1 antibody. Trace (c) depicts platelets incubated with 500 μM of the Random Peptide (SEQ ID NO:9), followed by 0.5 μM U46619 stimulation and FITC-PAC1 labeling. Trace (d) depicts platelets incubated with 150 μM of the $G_{13}SR2_{pep}$, followed by 0.5 μM U46619 stimulation and FITC-PAC1 labeling.

Subsequent experiments examined the effect of $G_{13}SR2_{pep}$, (SEQ ID NO:5) on human platelet $\alpha_{IIb}\beta_3$ integrin activation as measured by FITC-PAC-1 antibody binding. As shown in FIG. 6, addition of the TP agonist U46619 caused a large shift to the right (relative to resting platelets), demonstrating significant U46619-induced $\alpha_{IIb}\beta_3$ integrin activation. Furthermore, it was also found (FIG. 6) that compared to 500 µM of the Random Peptide control (SEQ ID NO:9), 150 µM $G_{13}SR2_{pep}$ dramatically inhibited this U46619-mediated activation of $\alpha_{IIb}\beta_3$ integrin. Similar inhibition was observed with platelet activation induced by the PAR1 receptor agonist TRAP1.

To further investigate the mechanism(s) by which $G_{13}SR2_{pep}$ (SEQ ID NO:5) inhibited $\alpha_{IIb}\beta_3$ integrin activation, the effect of $G_{13}SR2_{pep}$ on calcium flux, RhoA activation, Src activation and changes in cAMP levels was determined using conventional assays. These experiments demonstrated that $G_{13}SR2_{pep}$ (at a concentration more than sufficient to inhibit human platelet aggregation, i.e., 250 µM) did not alter calcium mobilization, RhoA or Src activation induced by TRAP1 (10 µM), U46619 (0.5 µM) or ADP (10 µM). Furthermore, this concentration of $G_{13}SR2_{pep}$ (250 µM) also did not alter cAMP levels in human platelet-rich plasma. These data therefore demonstrate that $G_{13}SR2_{pep}$ peptide (SEQ ID NO:5) acts downstream of these signaling pathways, e.g., by binding to and regulating $\alpha_{IIb}\beta_3$ integrin and/or its associated protein partners.

On this basis, subsequent experiments examined whether $G_{13}SR2_{pep}$ peptide (SEQ ID NO:5) does indeed directly interact with $\alpha_{IIb}\beta_3$ and/or one of its associated proteins in human platelets. In this respect, platelet $\alpha_{IIb}\beta_3$ integrin is known to exist in a complex with two cytoplasmic proteins, i.e., talin and kindlin-3 (Tadokoro, et al. (2003) Science 302:103-6; Moser, et al. (2008) Nature Med. 14:325-30). To determine whether $G_{13}SR2_{pep}$, (SEQ ID NO:5) interacts with any of these proteins (or with the entire $\alpha_{IIb}\beta_3$, talin, kindlin-3 complex), peptide affinity columns using $G_{13}SR2_{pep}$ (SEQ ID NO:5) were employed. The affinity purified protein(s) from solubilized human platelets that specifically bound to the $G_{13}SR2_{pep}$ peptide were eluted, and analyzed by western blot for $\alpha_{IIb}\beta_3$ integrin, talin and kindlin-3. In similar experiments, the eluates from a peptide column using the $G_{13}SR2$-Random Peptide (SEQ ID NO:9) were also analyzed. Immunoblot analysis with the $\alpha_{IIb}\beta_3$ antibodies (Abcam) detected two bands, one at 130 kD and the other at 115 kD in solubilized human platelets as well as in the elution fraction obtained from the $G_{13}SR2_{pep}$ (SEQ ID NO:5) affinity column. These results provide evidence that $\alpha_{IIb}\beta_3$ (or the $\alpha_{IIb}\beta_3$-talin-kindlin 3 complex) directly interacts with $G_{13}SR2_{pep}$. This was supported by similar experiments using talin antibodies and the kindlin 3 antibody (Abcam). These studies revealed that the $G_{13}SR2_{pep}$ (SEQ ID NO:5) also purified whole talin (220 kD), the talin head domain (47 kD) and kindlin 3 (72 kD). In contrast, eluates from the $G_{13}SR2$-Random Peptide (SEQ ID NO:9) control column did not reveal the presence of purified $\alpha_{IIb}\beta_3$, talin or kindlin 3.

Taken together these results demonstrate that a peptide representative of the conformationally sensitive switch region 2 (SR2) of $G\alpha_{13}$ directly interacts with the $\alpha_{IIb}\beta_3$-talin-kindlin 3 complex. Furthermore, when this complex is dissociated, analysis of affinity column eluates demonstrates that the binding partner, and hence the target for $G_{13}SR2_{pep}$ (SEQ ID NO:5), is the talin head domain. Thus, the binding of $G_{13}SR2_{pep}$ (SEQ ID NO:5) to the talin head domain serves as the basis for the ability of $G_{13}SR2_{pep}$ to inhibit $\alpha_{IIb}\beta_3$ integrin activation and platelet aggregation. As such, peptides or specific compounds fashioned to mimic or modify the switch region interaction with talin, $\alpha_{IIb}\beta_3$ integrin or other $\alpha_{IIb}\beta_3$ integrin-associated proteins would have profound effects on thrombosis and other integrin-linked disease processes. This is supported by the finding that administration of $G_{13}SR2_{pep}$ (Val-Gly-Gly-Gln-Arg-Ser-Glu-Arg-Lys-Arg-Trp-Phe-Glu-Cys-Phe-Asp-Ser; SEQ ID NO:5) substantially increases in vivo bleeding times in mice (see FIG. 7).

Accordingly, the present invention features compositions and methods for selectively inhibiting signaling of one or more Gα subunits with peptides or peptidomimetics by targeting the conformationally sensitive switch regions of these Gα subunits. In various embodiments, the Gα subunit is $G\alpha_s$, $G\alpha_{16}$, $G\alpha_z$, $G_{11}$, $G\alpha_{12}$, $G\alpha_o$, $G\alpha_{13}$, $G\alpha_q$ or $G\alpha_i$.

The peptides exemplified herein range in size from 9 to 17 amino acids. Accordingly, a peptide or peptidomimetic of the invention can be in the range of 9 to 40 amino acid residues and exhibits the ability to selectively inhibit signaling of one or more Gα subunits. In certain embodiments, a peptide or peptidomimetic of the invention is 9 to 30 amino acid residues, 9 to 25 amino acid residues or more desirably 9 to 20 amino acid residues in length. In particular embodiments, a peptide of the invention is a peptide listed in Table 1.

TABLE 1

| Gα subunit Target | Switch Region | Sequence | SEQ ID NO: |
|---|---|---|---|
| Gα$_{13}$ | SR1 | LLARRPTAGIHEY | 2 |
| | SR2 | VGGQRSERKRWFECFDS | 5 |
| Gα$_q$ | SR2 | VGGQRSERRKWIHCFEN | 3 |
| Gα$_i$ | SR2 | VGGQRSERKKWIHCFEG | 4 |
| Gα$_s$ | SR1 | RCRVLTSGIFETKFQVDK | 24 |
| | SR2 | VGGQRDERRKWIQCFND | 25 |
| Gα$_{16}$ | SR1 | RSRMPTTGI | 26 |
| | SR2 | VGGQKSERKKWIHCFEN | 27 |
| Gα$_z$ | SR1 | RSRDMTTGI | 28 |
| | SR2 | VGGQKSERKKWIHCFEN | 29 |

TABLE 1-continued

| Gα subunit Target | Switch Region | Sequence | SEQ ID NO: |
|---|---|---|---|
| Gα$_{11}$ | SR1 | RVRVPTTGI | 30 |
| Gα$_{12}$ | SR1 | LARKATKGI | 31 |
|  | SR2 | VGGQRSQRQKWFQCFDG | 32 |
| Gα$_o$ | SR1 | RTRVKTTGI | 33 |
|  | SR2 | VGGQRSERKKWIHCFED | 34 |

In other embodiments, the invention is a peptidomimetic of a peptide listed in Table 1. As is conventional in the art, a peptidomimetic is a small protein-like chain or non-peptide compound having the same three-dimensional structure as a peptide of this invention thereby mimicking the peptide. A peptidomimetic is typically produced by modification of an existing peptide in order to alter the molecule's properties. Such modifications can change the molecule's stability or biological activity. These modifications involve changes to the peptide that generally do not occur naturally (such as altered backbones and the incorporation of non-natural amino acids).

Also included within the scope of the invention are peptide fragments. A fragment of a peptide of this invention is intended to mean a 7 to 16 amino acid residue fragment, 8 to 15 amino acid residue fragment or 9 to 14 amino acid residue fragment of a peptide of listed in Table 1. Fragments can be produced by removing 1 to 7 amino acid residues of the C-terminus of the peptide, 1 to 7 amino acid residues of the N-terminus of the peptide, or 1 to 4 amino acid residues at the C- and N-terminus of the peptide. Examples of peptide fragments are listed in Table 2.

TABLE 2

| Gα subunit Target | Switch Region | Fragment Sequence | SEQ ID NO: |
|---|---|---|---|
| Gα$_{13}$ | SR1 | ARRPTAGIHEY | 12 |
|  |  | LLARRPTAGIH | 13 |
|  |  | ARRPTAGIHE | 14 |
|  | SR2 | RSERKRWFECFDS | 15 |
|  |  | VGGQRSERKRWFECF | 16 |
|  |  | RSERKRWFECFD | 11 |
| Gα$_q$ | SR2 | RSERRKWIHCFEN | 17 |
|  |  | VGGQRSERRKWIHCF | 18 |
|  |  | RSERRKWIHCFE | 19 |
| Gα$_i$ | SR2 | RSERKKWIHCFEN | 20 |
|  |  | VGGQRSERKKWIHCF | 21 |
|  |  | RSERKKWIHCFE | 22 |

As used herein, the term "peptide" also includes modified forms of the peptide, so long as the modification does not alter the essential sequence and the modified peptide retains the ability to inhibit signaling of a Gα subunit. Such modifications include N-terminal acetylation, glycosylation, biotinylation, etc. In a particular embodiment, a peptide, peptidomimetic or fragment of the invention can be modified to increase membrane permeability or the association of the peptide with cell membranes. Membrane permeability can be increased, e.g., by N-myristoylation (Brand, et al. (1996) *Am. J. Physiol. Cell. Physiol.* 270:C1362-C1369).

Similarly, the presence of an N-terminal D-amino acid can be used to increase the serum stability of a peptide or fragment which otherwise contains L-amino acids, because exopeptidases acting on the N-terminal residue cannot utilize a D-amino acid as a substrate (Powell, et al. (1993) *Pharmaceutical Res.* 10:1268-1273). Thus, the amino acid sequences of the peptides or fragments with N-terminal D-amino acids are usually identical to the sequences of the L-amino acid peptides or fragments, except that the N-terminal residue is a D-amino acid.

Moreover, the presence of a C-terminal D-amino acid can also stabilize a peptide or fragment, which otherwise contains L-amino acids, because serum exopeptidases acting on the C-terminal residue cannot utilize a D-amino acid as a substrate (Powell, et al. (1993) supra). Thus, the amino acid sequences of these peptides or fragments are usually identical to the sequences of the L-amino acid peptides or fragments, except that the C-terminal residue is a D-amino acid.

Cyclic peptides have no free N- or C-termini. Thus, they are not susceptible to proteolysis by exopeptidases, although they are of course susceptible to endopeptidases, which do not cleave at peptide termini. The amino acid sequences of cyclic peptides or fragments may be identical to the sequences of the L-amino acid peptides or fragments, except that the topology is circular, rather than linear.

Substitution of unnatural amino acids for natural amino acids in a subsequence of a peptide or fragment of the invention can also confer resistance to proteolysis. Such a substitution can, for example, confer resistance to proteolysis by exopeptidases acting on the N-terminus. Such substitutions have been described and these substitutions do not affect biological activity. The synthesis of peptides with unnatural amino acids is routine and known in the art (Coller, et al. (1993) *J. Biol. Chem.* 268:20741-20743).

An effective approach to confer resistance to peptidases acting on the N-terminal or C-terminal residues of a peptide or fragment is to add chemical groups at the peptide termini, such that the modified peptide or fragment is no longer a substrate for the peptidase. One such chemical modification is glycosylation of the peptides or fragments at either or both termini. Certain chemical modifications, in particular N-terminal glycosylation, have been shown to increase the stability of peptides in human serum (Powell et al. (1993) *Pharma. Res.* 10:1268-1273). Other chemical modifications which enhance serum stability include, but are not limited to, the addition of an N-terminal allyl group, composed of a lower alkyl of from 1 to 20 carbons, such as an acetyl group, and/or the addition of a C-terminal amide or substituted amide group.

The peptides and fragments of this invention, including modified peptides, can generally be prepared following known techniques. Preferably, synthetic production of a peptide or fragment of the invention may be according to the solid phase synthetic method. For example, the solid phase synthesis is well understood and is a common method for preparation of peptides, as are a variety of modifications of that technique (Merrfield (1964) *J. Am. Chem. Soc.* 85:2149; Stewart & Young (1984) *Solid Phase Peptide Synthesis*, Pierce Chemical Company, Rockford, Ill.; Bodansky & Bodanszky (1984) *The Practice of Peptide Synthesis*, Springer-Verlag, New York; Atherton & Sheppard (1989) *Solid-Phase Peptide Synthesis: A Practical Approach*, IRL Press, New York).

Alternatively, peptides or fragments of this invention may be prepared in recombinant systems using polynucleotide sequences encoding the peptides or fragments. It is understood that a peptide or fragment of this invention may contain more than one of the above described modifications within the same peptide or fragment. Also included in this invention are pharmaceutically acceptable salt complexes of the peptides or fragments of this invention.

As indicated above, a peptidomimetic is a molecule that mimics the biological activity of a peptide. By strict definition, a peptidomimetic is a molecule that no longer contains any peptide bonds (that is, amide bonds between amino acids). However, the term peptidomimetic is sometimes used to describe molecules that are no longer completely peptidic in nature, such as pseudo-peptides, semi-peptides and peptoids. Examples of some peptidomimetics by the broader definition (where part of a peptide is replaced by a structure lacking peptide bonds) are described herein. Whether completely or partially non-peptide, peptidomimetics according to this invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems which are similar to the biological activity of the peptide.

The present invention encompasses peptidomimetic compositions which are analogs that mimic the activity of biologically active peptides according to the invention, i.e., the peptidomimetics are capable of inhibiting Gα protein signaling. A peptidomimetic of this invention is preferably substantially similar in both three-dimensional shape and biological activity to the peptides set forth herein. Substantial similarity means that the geometric relationship of groups in the peptide that react with (or mimic) the Gα subunit is preserved and at the same time, that the peptidomimetic will selectively inhibit Gα protein signaling.

There are clear advantages for using a mimetic of a given peptide. For example, there are considerable cost savings and improved patient compliance associated with peptidomimetics, since they can be administered orally compared with parenteral administration for peptides. Furthermore, peptidomimetics are much cheaper to produce than peptides.

Thus, peptides described above have utility in the development of such small chemical compounds with similar biological activities and therefore with similar therapeutic utilities. The techniques of developing peptidomimetics are conventional. Thus, peptide bonds can be replaced by non-peptide bonds that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide, either free or bound to a Gα protein (or a Gα protein effector), by NMR spectroscopy, crystallography and/or computer-aided molecular modeling. These techniques aid in the development of novel compositions of higher potency and/or greater bioavailability and/or greater stability than the original peptide (Dean (1994) *BioEssays* 16:683-687; Cohen & Shatzmiller (1993) *J. Mol. Graph.* 11:166-173; Wiley & Rich (1993) *Med. Res. Rev.* 13:327-384; Moore (1994) *Trends Pharmacol. Sci.* 15:124-129; Hruby (1993) *Biopolymers* 33:1073-1082; Bugg, et al. (1993) *Sci. Am.* 269:92-98). Once a potential peptidomimetic compound is identified, it may be synthesized and assayed using an assay described herein or any other appropriate assay for monitoring Gα protein signaling.

Thus, through use of the methods described herein, the present invention embraces compounds exhibiting enhanced therapeutic activity. The peptidomimetic compounds obtained by the above methods, having the biological activity of the above named peptides and similar three dimensional structure, are encompassed by this invention. It will be readily apparent to one skilled in the art that a peptidomimetic can be generated from any of the modified peptides exemplified herein. It will furthermore be apparent that the peptidomimetics of this invention can be further used for the development of even more potent non-peptidic compounds, in addition to their utility as therapeutic compounds.

Proteases act on peptide bonds. It therefore follows that substitution of peptide bonds by pseudopeptide bonds confers resistance to proteolysis. A number of pseudopeptide bonds have been described that in general do not affect peptide structure and biological activity. The reduced isostere pseudopeptide bond is a suitable pseudopeptide bond that is known to enhance stability to enzymatic cleavage with no or little loss of biological activity (Couder, et al. (1993) *Int. J. Peptide Protein Res.* 41:181-184). Thus, the amino acid sequences of such peptides may be identical to the sequences of the L-amino acid peptides, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993) supra).

To confer resistance to proteolysis, peptide bonds may also be substituted by retro-inverso pseudopeptide bonds (Dalpozzo, et al. (1993) *Int. J. Peptide Protein Res.* 41:561-566). According to this modification, the amino acid sequences of the peptides may be identical to the sequences of the L-amino acid peptides, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. The synthesis of peptides with one or more reduced retro-inverso pseudopeptide bonds is known in the art (Dalpozzo, et al. (1993) supra).

Peptoid derivatives of peptides represent another form of modified peptides that retain the important structural determinants for biological activity, yet eliminate the peptide bonds, thereby conferring resistance to proteolysis (Simon, et al. (1992) *Proc. Natl. Acad. Sci. USA* 89:9367-9371). Peptoids are oligomers of N-substituted glycines. A number of N-alkyl groups have been described, each corresponding to the side chain of a natural amino acid (Simon, et al. (1992) supra).

The ability of the above-described peptides, peptidomimetics, fragments and compositions of this invention to selectively inhibit Gα subunit signaling and thus cellular functions associated with a particular Gα subunit (e.g., platelet aggregation or $\alpha_{IIb}\beta_3$ integrin activation), enables their use as pharmaceutical compositions in a variety of therapeutic regimens. The present invention therefore includes novel therapeutic pharmaceutical compositions and methods for treating a human or animal with such compositions. As used herein, the term "pharmaceutical" includes veterinary applications of the invention.

To prepare the pharmaceutical compositions of the present invention, at least one peptide (or peptidomimetic or fragment), or alternatively, a mixture of peptides (or peptidomimetics or fragments) of this invention is combined as the active ingredient in admixture with a pharmaceutically acceptable carrier selected and prepared according to conventional pharmaceutical compounding techniques. This carrier may take a wide variety of forms depending on the form of preparation desired for administration, e.g., oral, sublingual, rectal, nasal, or parenteral.

Pharmaceutically acceptable solid or liquid carriers or components which may be added to enhance or stabilize the composition, or to facilitate preparation of the composition include, without limitation, syrup, water, isotonic saline solution, 5% dextrose in water or buffered sodium or ammonium acetate solution, oils, glycerin, alcohols, flavoring agents, preservatives, coloring agents starches, sugars, diluents, granulating agents, lubricants, and binders, among others. The carrier may also include a sustained release material such as glyceryl monostearate or glyceryl distearate, alone or with a wax. The amount of solid carrier varies but, preferably will be between about 20 mg to about 1 g per dosage unit.

Pharmaceutical compositions of the peptides, peptidomimetics, or fragments of this invention may therefore be formulated as solutions of lyophilized powders for parenteral administration.

Pharmaceutical compositions of this invention may also include topical formulations incorporated in a suitable base or vehicle, for application at the site of the area for the exertion of local action. Accordingly, such topical compositions include those forms in which the formulation is applied externally by direct contact with the skin surface to be treated. Conventional forms for this purpose include but are not limited to creams, ointments, lotions, gels, pastes, powders and formulations having oleaginous absorption, water-soluble, and emulsion-type bases.

Additionally, the molecules of the present invention may also be administered encapsulated in liposomes. The composition, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such a diacetylphosphate, stearylamine, or phosphatidic acid, and/or other materials of a hydrophobic nature.

The compositions may be supplemented by active pharmaceutical ingredients, where desired. Optional antibacterial, antiseptic, and antioxidant agents may also be present in the compositions where they will perform their ordinary functions.

Dosage units of such pharmaceutical compositions containing the peptides or peptidomimetic compounds of this invention preferably contain about 1 mg to 5 g of the peptide or salt thereof.

As used herein, the term "effective amount" means an amount which is effective to prevent, treat, mitigate, attenuate or ameliorate the conditions referred to herein. An effective amount of a peptide, peptidomimetic, or fragment of the present invention can be readily determined by the skilled clinician based upon amounts of similar compounds employed in current treatment regimes, studies in suitable animal models or clinical trials.

The pharmaceutical compositions described herein as possessing the ability to inhibit Gα protein signaling are useful in therapeutic regimens which exploit the cellular functions of one or more specific Gα proteins. In this respect, the compositions of the invention can be administered to subjects in need of treatment so that Gα protein signaling is decreased, inhibited or attenuated in the subject as determined, e.g., by the expression or activity of proteins downstream of Gα protein signaling (e.g., $\alpha_{11b}\beta_3$ integrin), or alternatively based upon the prevention, attenuation, decrease, inhibition or reduction in the signs or symptoms of the disease being treated, (e.g., a decrease in an undesirable or excessive amount of platelet aggregation).

Diseases or condition that can be prevented or treated in accordance with this invention include, but are not limited to, cancer, asthma, hypertension, HIV-1 infection, hepatocyte injury, thromboembolic peripheral disease, thromboembolic stroke, coronary thromboembolism, and other integrin-dependent disease processes. For example, signaling through the heterotrimeric G proteins ($G\alpha_{12}$ and $G\alpha_{13}$) has been shown to promote breast cancer cell invasion (Kelly, et al. (2006) *Proc. Natl. Acad. Sci. USA* 103(21):8173-8), such that inhibition of $G_{\alpha 13}$ signaling, e.g., with a peptide or peptidomimetic of the structure set forth in SEQ ID NO:2, would be expected to reduce the metastatic dissemination of breast cancer cells in vivo. Furthermore, up-regulation of $G\alpha_q$ protein has been suggested as being involved in the pathogenesis of bronchial smooth muscle hyperresponsiveness, one of the causes of airway hyperresponsiveness in asthmatics (Chiba, et al. (2008) *J. Smooth Muscle Res.* 44(2):95-100), wherein inhibition of $G\alpha_q$ signaling, e.g., with a peptide or peptidomimetic of the structure set forth in SEQ ID NO:3, would be useful in the treatment of asthma. Moreover, data from human and animal studies indicate that $G\alpha_q$ signaling is important for blood pressure regulation (Harris, et al. (2007) *Am. J. Physiol. Heart. Circ. Physiol.* 293(5):H3072-9), such that inhibition of $G\alpha_q$ signaling would be useful in antihypertensive therapy. In addition, local administration of a $G\alpha_{q/11}$ inhibitor has been suggested as being useful treating peripheral arterial disease including thrombosis (Uemura, et al. (2006) *Eur. J. Pharmacol.* 536(1-2):154-61; Kawasaki, et al. (2005) *Thromb. Haemost.* 94(1):184-92). Moreover, $G_{\alpha i}$ protein has been shown to be involved in HIV-1 infectability (Lin, et al. (2006) *AIDS* 20:1369-1377), such that inhibition of $G_{\alpha i}$, with a peptide or peptidomimetic of SEQ ID NO:4, would be useful in inhibiting or reducing HIV-infection. Furthermore, inhibition of $G_{\alpha i}$ has been suggested to be useful in the prevention and/or treatment of hepatocyte injury in nonalcoholic steatohepatitis (Han, et al. (2008) *J. Lipid Res.* 49(1):84-97). Moreover, administration of a peptide or peptidomimetic of SEQ ID NO:5 or SEQ ID NO:11 would provide universal inhibition of platelet aggregation and $\alpha_{11}\beta_3$ integrin activation for use in the treatment of thromboembolic peripheral disease, thromboembolic stroke, and coronary thromboembolism.

What is claimed is:

1. A Gα peptide, wherein said Gα peptide consists of SEQ ID NO: 2-5, 11-22 or 24-34.

2. The Gα peptide of claim 1, wherein the Gα peptide comprises an acetylation, glycosylation, biotinylation, or myristoylation.

3. A method for inhibiting Gα subunit signaling comprising contacting a cell with the Gα peptide of claim 1, thereby inhibiting Gα subunit signaling in the cell.

4. A method for inhibiting Gα subunit signaling comprising contacting a cell with the Gα peptide of claim 2, thereby inhibiting Gα subunit signaling in the cell.

* * * * *